(12) United States Patent
Williams (10) Patent No.: US 11,103,242 B2
(45) Date of Patent: Aug. 31, 2021

(54) CHIP ASSEMBLY FOR SURGICAL INSTRUMENTS

(71) Applicant: Covidien LP, Mansfield, MA (US)

(72) Inventor: Justin Williams, Southbury, CT (US)

(73) Assignee: Covidien LP, Mansfield, MA (US)

( * ) Notice: Subject to any disclaimer, the term of this patent is extended or adjusted under 35 U.S.C. 154(b) by 117 days.

(21) Appl. No.: 16/671,678

(22) Filed: Nov. 1, 2019

(65) Prior Publication Data
US 2020/0060678 A1 Feb. 27, 2020

Related U.S. Application Data

(62) Division of application No. 14/056,301, filed on Oct. 17, 2013, now Pat. No. 10,463,365.

(51) Int. Cl.
*A61B 17/068* (2006.01)
*A61B 17/115* (2006.01)
(Continued)

(52) U.S. Cl.
CPC ........ *A61B 17/068* (2013.01); *A61B 17/1155* (2013.01); *A61B 90/98* (2016.02); *A61B 2017/00477* (2013.01)

(58) Field of Classification Search
CPC . A61B 17/068; A61B 17/105; A61B 17/1155; A61B 90/98; A61B 2017/00477; A61B 2017/07271; A61B 2017/07214
See application file for complete search history.

(56) References Cited

U.S. PATENT DOCUMENTS 4,576,167 A * 3/1986 Noiles .................. A61B 17/115
227/179.1
4,603,693 A * 8/1986 Conta ................. A61B 17/1155
227/179.1
(Continued)

FOREIGN PATENT DOCUMENTS

CN 103445815 A 12/2013
EP 2308388 A1 4/2011
(Continued)

OTHER PUBLICATIONS

Maxim Integrated Brochure (Abridged Data Sheet)—DeepCover Secure Authenticator with 1-Wire SHA-256 and 512-Bit User EEPROM, pp. 1-4 and p. 42, 2012.
(Continued)

*Primary Examiner* — Thomas M Wittenschlaeger
(74) *Attorney, Agent, or Firm* — Carter, DeLuca & Farrell LLP (57) ABSTRACT

A surgical stapling device is provided. The surgical stapling device includes a handle assembly, an adapter assembly removably and selectively attachable to the handle assembly, and a loading unit removably and selectively attachable to the adapter assembly. The adapter assembly extends from the handle assembly for transmitting actuating forces from the handle assembly to the loading unit. The adapter assembly includes a connector assembly. The loading unit includes a shell member and a housing extending from an inner surface of the shell member. The surgical stapling device further includes a chip assembly disposed within the housing and moveable relative to the shell member to facilitate connection with the connector assembly of the adapter assembly.

12 Claims, 8 Drawing Sheets

(51) Int. Cl.
*A61B 90/98* (2016.01)
*A61B 17/00* (2006.01)

(56) References Cited

U.S. PATENT DOCUMENTS

| | | | |
|---|---|---|---|
| 4,731,058 A | 3/1988 | Doan | |
| 5,391,166 A | 2/1995 | Eggers | |
| 5,699,406 A * | 12/1997 | Liikanen | G06K 7/0021 |
| | | | 379/357.01 |
| 7,721,931 B2 | 5/2010 | Shelton, IV et al. | |
| 7,887,530 B2 | 2/2011 | Zemlok et al. | |
| 8,118,206 B2 * | 2/2012 | Zand | A61B 5/14556 |
| | | | 227/175.1 |
| 8,397,971 B2 | 3/2013 | Yates et al. | |
| 10,463,365 B2 | 11/2019 | Williams | |
| 2002/0109976 A1* | 8/2002 | Villain | G06K 7/0021 |
| | | | 361/801 |
| 2006/0216023 A1* | 9/2006 | Tokiwa | G03B 17/02 |
| | | | 396/532 |
| 2007/0196100 A1* | 8/2007 | Miyake | H04N 5/23245 |
| | | | 396/342 |
| 2007/0221497 A1* | 9/2007 | Egawa | G01N 33/491 |
| | | | 204/403.01 |
| 2008/0002968 A1* | 1/2008 | Aral | G03B 17/14 |
| | | | 396/448 |
| 2008/0139959 A1* | 6/2008 | Miethke | A61B 5/031 |
| | | | 600/561 |
| 2009/0057369 A1 | 3/2009 | Smith et al. | |
| 2009/0090763 A1 | 4/2009 | Zemlok et al. | |
| 2009/0108048 A1* | 4/2009 | Zemlok | A61B 17/00234 |
| | | | 227/175.1 |
| 2010/0136816 A1* | 6/2010 | Ahn | G06K 7/0021 |
| | | | 439/331 |
| 2011/0022032 A1* | 1/2011 | Zemlok | A61B 17/07207 |
| | | | 606/1 |
| 2011/0095067 A1* | 4/2011 | Ohdaira | A61B 17/07207 |
| | | | 227/175.2 |
| 2011/0095070 A1* | 4/2011 | Patel | A61B 17/105 |
| | | | 227/181.1 |
| 2011/0155784 A1 | 6/2011 | Shelton, IV et al. | |

FOREIGN PATENT DOCUMENTS

| | | |
|---|---|---|
| EP | 2324776 A2 | 5/2011 |
| EP | 2329773 A1 | 6/2011 |
| EP | 2823774 A2 | 1/2015 |
| EP | 2839797 A2 | 2/2015 |
| JP | 679093 | 4/1994 |
| JP | 2013150877 A | 8/2013 |

OTHER PUBLICATIONS

"IC-On-Line" DS28E15-1-Wire SHA-256 Secure Authenticator with 512-Bit User EEPROM, located at: <http://www.ic-on-line.cn/view_download>.
Extended European Search Report corresponding to 14 18 9145.7 dated Apr. 29, 2015.
Chinese Office Action dated Jan. 26, 2018 issued in CN Application No. 2014105544223.
Japanese Office Action dated Apr. 23, 2018 in JP Appln. No. 2014207846.

* cited by examiner

CHIP ASSEMBLY FOR SURGICAL INSTRUMENTS

CROSS REFERENCE TO RELATED APPLICATION

This application is a divisional of U.S. patent application Ser. No. 14/056,301, filed Oct. 17, 2013, the entire disclosure of which is incorporated by reference herein.

BACKGROUND

Technical Field

The present disclosure relates to surgical instruments having a handle assembly and an end effector. More particularly, the present disclosure relates to a loading unit including a chip assembly for use with a handle assembly.

Background of Related Art

Powered surgical instruments for use in endoscopic procedures are known. Typically, such instruments include a reusable handle assembly and a disposable end effector. An adapter assembly connects the end effector to the handle assembly and is configured to transfer mechanical and/or electrical forces from the handle assembly to the end effector. In the case of a surgical stapler, the end effector includes a disposable cartridge or loading unit that is changed after each firing of the surgical stapler. To reduce costs and shorten procedure times, the handle assembly is generally configured for use with a variety of loading units of various configurations for use on tissue having different properties, i.e., thickness, density. For example, different loading units may have staples of different sizes and/or the staples may be arranged in different configurations. To ensure the handle assembly is programmed to operate with the attached loading unit, some loading units are provided with a chip that communicates the configuration of the loading unit to the handle assembly. Information regarding the configuration of the loading unit is automatically relayed to the handle assembly upon attachment of the loading unit to the adapter assembly (that has been pre-attached to the handle assembly). In this manner, when switching between loading units of different configurations the programming of the handle assembly is automatically accomplished.

Space within the loading unit is limited. In addition, improper alignment between the chip assembly located in the loading unit and the connector assembly located in the adapter assembly of the surgical stapler may prevent the information relating to the configuration of the loading unit from being relayed to the handle assembly. Such misalignment of the chip assembly and connector may result in less then optimal performance of the surgical stapler.

Therefore, it would be beneficial to have a loading unit for use with a surgical stapler, wherein the loading unit includes a chip assembly configured to facilitate selective connection with an adapter assembly of the surgical stapler.

SUMMARY

In accordance with an aspect of the present invention a surgical stapling device comprises a handle assembly, and an adapter assembly removably and selectively attachable to the handle assembly and extending from the handle assembly. The adapter assembly includes a connector assembly and is configured to transmit actuating forces from the handle assembly. A loading unit is removably and selectively attachable to the connector assembly of the adapter assembly, the loading unit including a shell member and a housing extending from an inner surface of the shell member. A memory chip assembly is disposed within the housing of the loading unit and is moveable relative to the shell member to facilitate connection with the connector assembly of the adapter assembly.

The chip assembly may include a chip member and a spring member. In certain embodiments, the spring member biases the chip member radially inward. The spring member can include a leaf-spring for biasing the chip member.

The housing may include a lip for retaining the chip assembly within a recess formed by the housing. The lip may define an opening for selectively receiving a portion of the chip assembly therethrough. The shell member can define a cutout for radially loading the chip assembly into the recess formed by the housing. The housing can be configured to permit axial loading of the chip assembly within the recess formed by the housing.

In certain embodiments, the chip assembly includes a plurality of connection protrusions configured to engage a plurality of connection plates formed on the connector assembly when the loading unit is attached to the adapter assembly. In certain embodiments, the loading unit is configured to be secured to the adapter assembly by a bayonet coupling.

In certain embodiments, the chip assembly includes a chip configured to relay a configuration of the loading unit to the handle assembly. The connector assembly may be secured to a distal end of the adapter assembly.

BRIEF DESCRIPTION OF THE DRAWINGS

The accompanying drawings, which are incorporated in and constitute a part of this specification, illustrate embodiments of the disclosure and, together with a general description of the disclosure given above, and the detailed description of the embodiments given below, serve to explain the principles of the disclosure, wherein.

DETAILED DESCRIPTION

Embodiments of the presently disclosed loading units including a chip assembly will now be described in detail with reference to the drawings in which like reference numerals designate identical or corresponding elements in each of the several views. As is common in the art, the term "proximal" refers to that part or component closer to the user or operator, i.e. surgeon or clinician, while the term "distal" refers to that part or component further away from the user.

Figure 1:
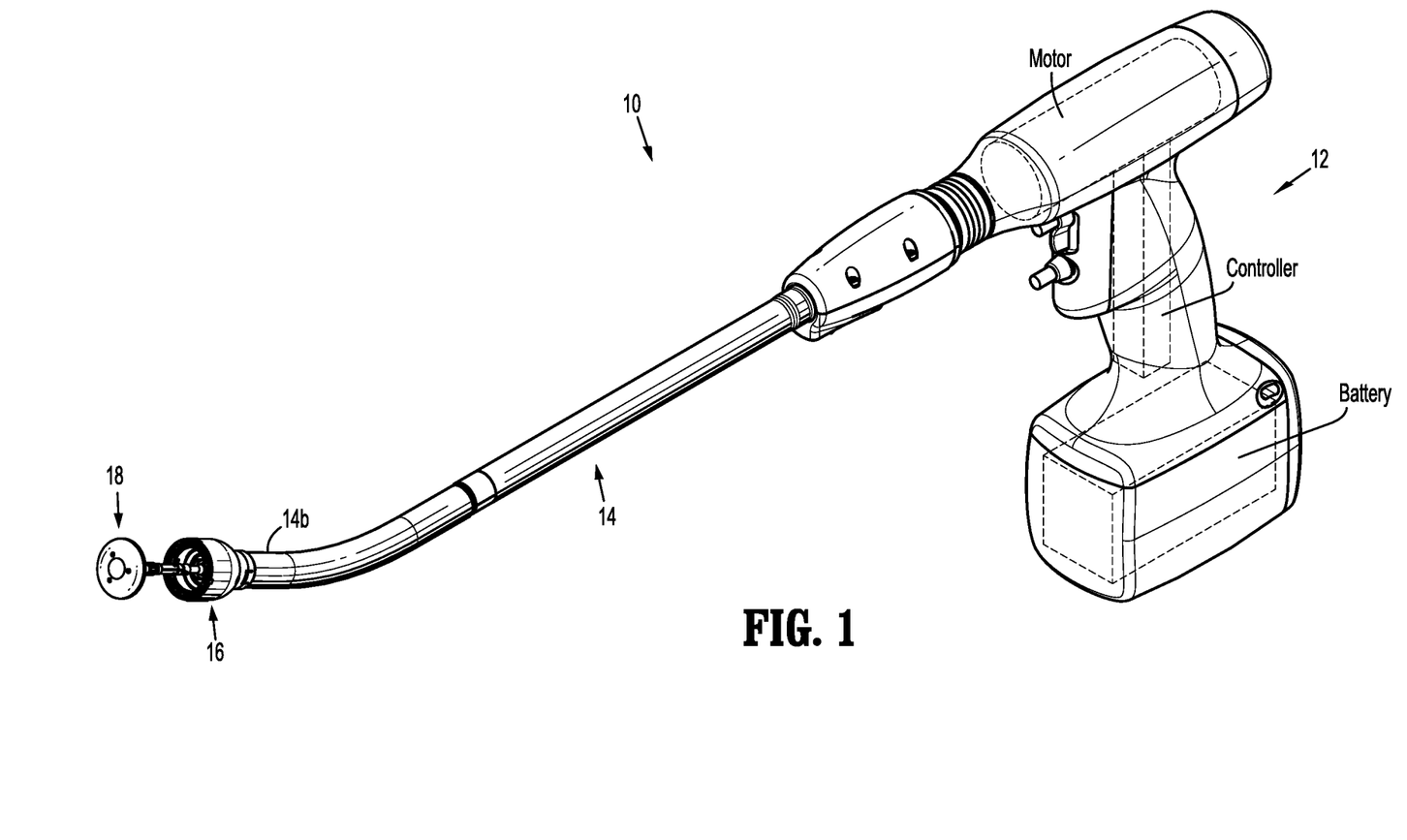
FIG. 1 is a perspective view of a surgical stapling device including a loading unit having a chip assembly according to embodiments of the present disclosure.

With reference initially to FIG. 1, a surgical stapling instrument including a loading unit having a chip assembly according to the present disclosure is shown generally as circular stapler 10. Circular stapler 10 includes a handle assembly 12, an adapter assembly 14 selectively securable and extending distally from handle assembly 12, and a loading unit 16 selectively securable to a distal end 14b of adapter assembly 14. An anvil member 18 is releasably secured to circular stapler 10. The adapter assembly 14 is configured to directly transmit and/or convert a rotational force of each rotatable drive shaft (not shown) of handle assembly 12 into additional rotational forces and/or axial translational forces useful for operating loading unit 16. A detailed description of an exemplary handle assembly 12 and adapter assembly 14 is provided in commonly owned U.S. Patent Appl. Publ. No. 2012/0089131, the content of which is hereby incorporated herein by reference in its entirety.

Although the chip assemblies of the present disclosure will be described with reference to a powered, hand-held, electromechanical surgical circular stapler 10, it is envisioned that the chip assemblies of the present disclosure may be modified for use with any instrument. The loading unit 16 and/or adapter assembly 14 may be configured for use with an electromechanical powered handle and/or console or surgical robot (having a remote power source and/or motor and/or integral or remote computerized control), in any of the embodiments disclosed herein. Other configurations are contemplated, such as, for example, a loading unit 16 attached to a shaft assembly that is not removable.

Figure 2:
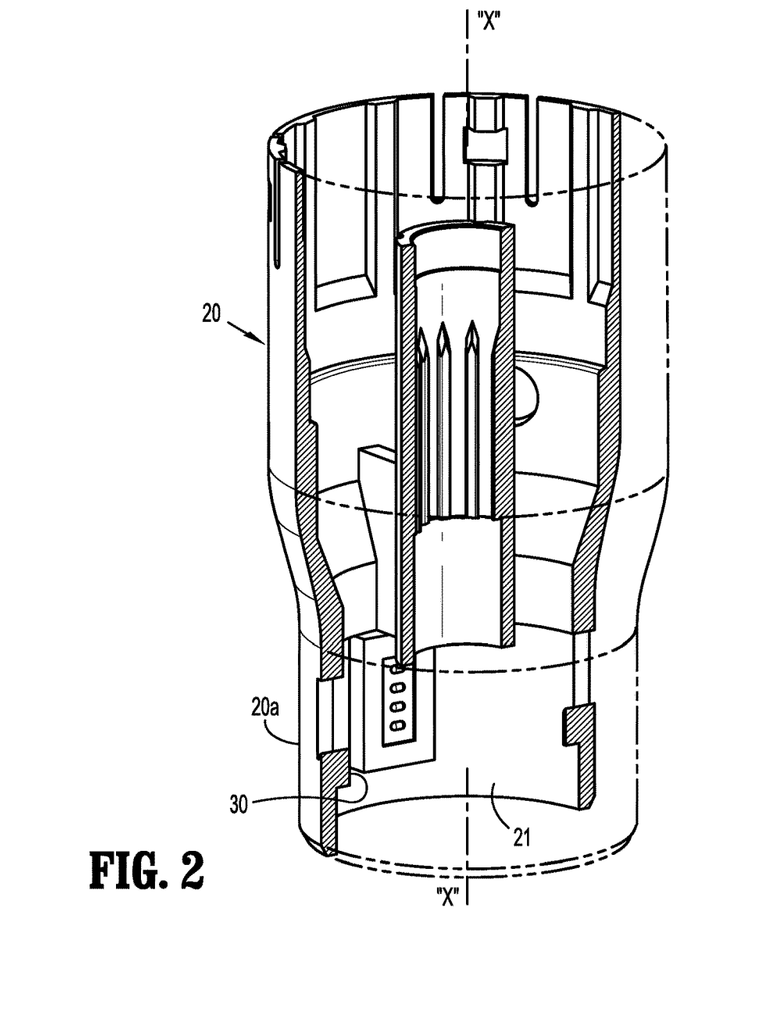
FIG. 2 is a partial longitudinal cross-sectional perspective view of the loading unit of the surgical stapling device shown in FIG. 1.
Figure 3:
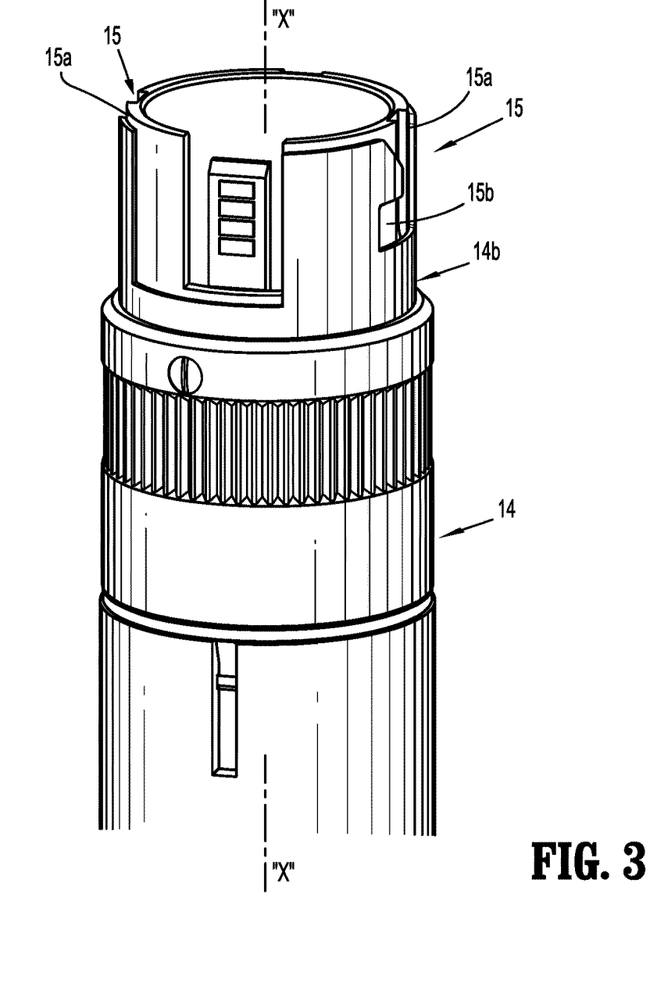
FIG. 3 is an enlarged partial perspective view of a distal end of an adapter assembly of the surgical stapling device shown in FIG. 1, including a connector assembly.

Referring now to FIGS. 1-3, loading unit 16 includes a shell member 20. A proximal end 20a of shell member 20 is selectively securable to distal end 14b of adapter assembly 14 of circular stapler 10. As shown, shell member 20 is secured to adapter assembly 14 of circular stapler 10 with a slot and tab configuration known as a bayonet coupling. In particular, a plurality of tabs 22 extend radially inward from an inner surface 21 of shell member 20 and are configured to be selectively received in corresponding L-shaped slots 15 (FIG. 3) formed in distal end 14b of adapter assembly 14. L-shaped slots 15 include an elongated portion 15a extending parallel to longitudinal axis "x" and a shortened portion 15b extending perpendicular or transverse to longitudinal axis "x".

As will be described in further detail below, attaching of shell member 20 of loading unit 16 to adapter assembly 14 of circular stapler 10 includes advancing shell member 20 axially relative to adapter assembly 14 such that proximal end 20a of shell member 20 is received about distal end 14b of adapter assembly 14 and tabs 22 of shell member 20 are fully received within elongated portion 15a of L-shaped slots 15 of adapter assembly 14. Once tabs 22 of shell member 20 are fully received within elongated portions 15a of L-shaped slots 15, shell member 20 is secured to adapter assembly 14 by moving shell member 20 along longitudinal axis "x" (FIG. 9) relative to adapter assembly 14 such that tabs 22 are received within shortened portions 15b of L-shaped slots 15. Although shown as being connected using a bayonet coupling, it is envisioned that shell member 20 and adapter assembly 14 of circular stapler 10 may be connected in any suitable manner. For example, loading unit 16 may be selectively secured to distal end 14b of adapter assembly 14 in the manner described in Chinese Patent Application Serial No. 201310084378.X, the content of which is hereby incorporated herein by reference in its entirety.

Figure 4:
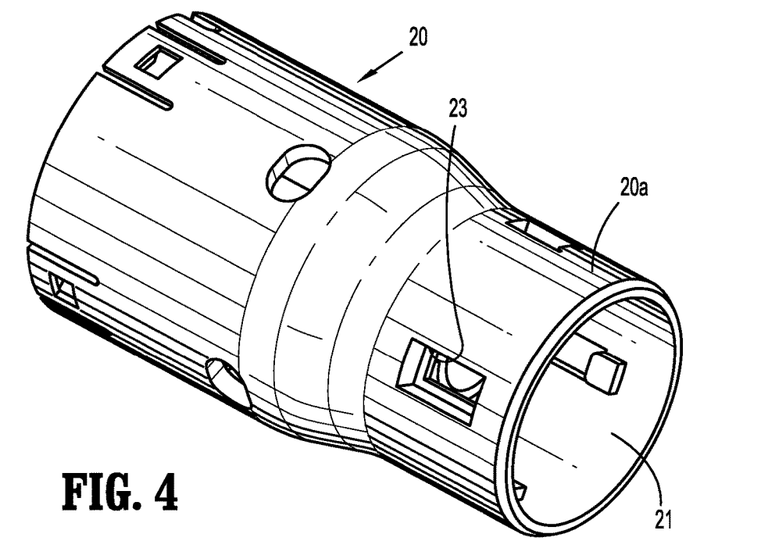
FIG. 4 is a perspective view of the loading unit shown in FIGS. 1 and 2.
Figure 5:
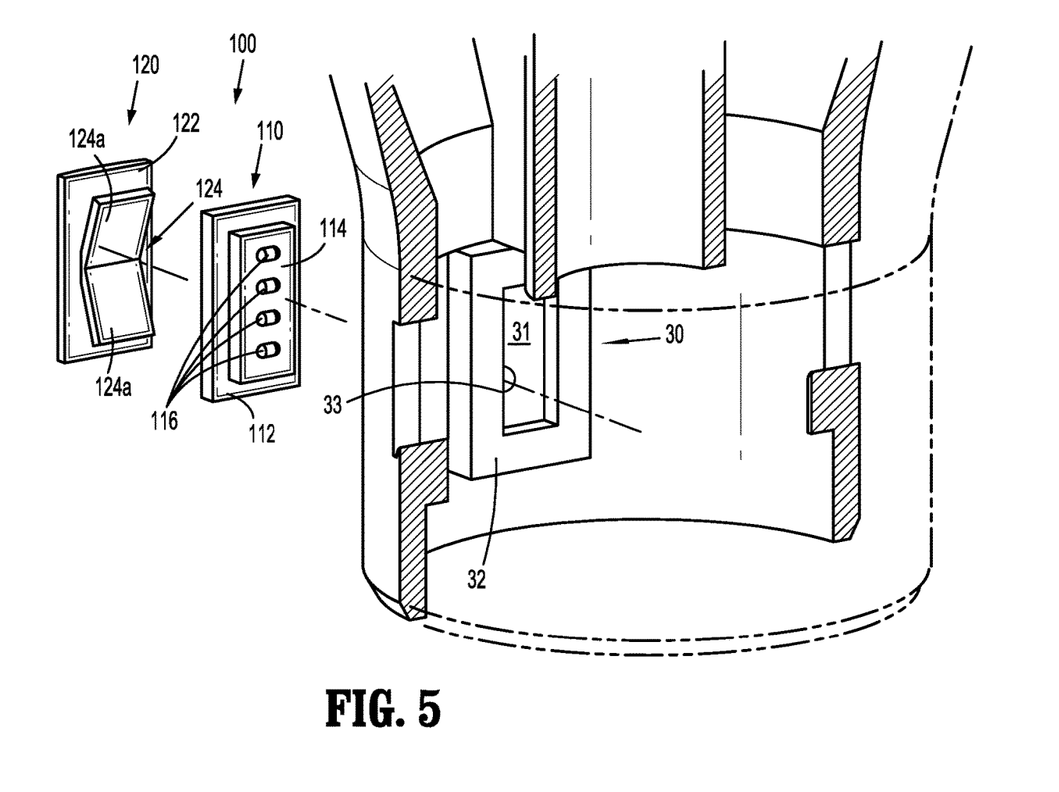
FIG. 5 is an enlarged partial, longitudinal cross-sectional perspective view of a proximal end of the loading unit shown in FIG. 1 including an exploded view of a chip assembly according to an embodiment of the present disclosure.

With reference now to FIGS. 4 and 5, proximal end 20a of shell member 20 defines a cutout 23 and includes a housing 30 formed about cutout 23. Cutout 23 is configured to permit external loading of a chip assembly 100 into a recess 31 formed by housing 30. Although shown having a rectangular shape, it is envisioned that cutout 23 and recess 31 may include alternative configurations.

Housing 30 includes a lip 32 formed about recess 31 for retaining chip assembly 100 within recess 31. (See FIG. 5). Lip 32 defines an opening 33 for providing access to chip assembly 100 from within shell member 20 when chip assembly 100 is received within recess 31 of housing 30. Housing 30 is positioned within shell member 20 such that, upon attachment of loading unit 16 to distal end 14b of adapter assembly 14, chip assembly 100 aligns with a connector assembly 130 (FIG. 8) mounted to distal end 14b of adapter assembly 14. As described above, attachment of loading unit 16 to adapter assembly 14 requires both axial and rotational movement of shell member 20 of loading unit 16 and distal end 14b of adapter assembly 14 relative to each other. Thus, as will be described in further detail below, housing 30 of loading unit 16 is positioned within shell member 20 to align with connector assembly 130 within adapter assembly 14 subsequent to axial and rotational movement of shell member 20 relative to adapter assembly 14.

With reference still to FIG. 5, chip assembly 100 includes a chip member 110 and a spring member 120. Chip member 110 includes a base portion 112 and a chip 114. Base portion 112 forms a planar member configured to be received within recess 31 of housing 30 formed on shell member 20. As will be described in further detail below, base portion 112 is configured to permit radial movement (i.e., toward and away from the center of the housing 30) of chip member 110 within recess 31 of housing 30 to facilitate connection between chip assembly 100 and connector assembly 130. Although shown having a substantially rectangular shape, base portion 112 may include any shape suitable for reception through cutout 23 in shell member 20 and within recess 31 of housing 30.

Chip 114 may include any commercially available chip capable of storing the specifications of loading unit 16, e.g., cartridge size, staple arrangement, staple length, clamp-up distance, production date, model number, lot number, expiration date, etc., and transmitting at least some of the information to handle assembly 12. In one embodiment, chip 114 includes an erasable programmable read only memory ("EPROM") chip. In this manner, the configuration of an attached loading unit may be relayed to handle assembly 12 such that, for example, the firing forces and/or the length of the firing stroke of handle assembly 12 may be adjusted to accommodate the particular loading unit 16. It is further envisioned that instead of an EPROM, chip 114 may be a read/write memory chip, such as read/write RAM, such that data may be written to chip 114, for example usage information that a loading unit has been fully or partially fired to prevent reuse of an empty or partially fired loading unit, or for any other purpose. Such a chip may also store the information discussed above.

Chip 114 is sized to be received through opening 33 defined by lip 32 of housing 30 formed on shell member 20. Chip 114 includes a plurality of connection protrusions 116. As will be described in further detail below, connection protrusions 116 include a rounded profile configured to facilitate engagement and alignment of connection protrusions 116 with connection plates 136 formed on extension portion 132 of connector assembly 130. It is envisioned that connection protrusions 116 may instead have a tapered profile or be otherwise configured to facilitate engagement and alignment with connection plates 136 formed on extension portion 132 of connector assembly 130. As shown, chip 114 includes four (4) connection protrusions 116, however, it is envisioned that chip 114 may include more or less than four (4) connection protrusions 116.

Still referring to FIG. 5, spring member 120 of chip assembly 100 includes a support portion 122 and a biasing portion 124. Support portion 122 and biasing portion 124 may be monolithically formed, as shown, however, it is envisioned that support portion 122 and biasing portion 124 may be formed as separate members. When formed as separate members, support portion 122 and biasing portion 124 may be joined together using adhesive, welding, mechanical fasteners or any other suitable method. In some embodiments, biasing portion 124 remains detached from support portion 122.

Support portion 122 of spring member 120 is configured to be received within cutout 23 of shell member 20 such that biasing portion 124 extends within recess 31 of housing 30. As shown, support portion 122 defines a substantially rectangular member configured to be received within cutout 23. Support portion 122 may include any configuration suitable for reception within cutout 23. Support portion 122 may be fixedly secured to shell member 20 within cutout 23, e.g., through friction-fit, welding, adhesives, mechanical fasteners or by any other suitable method. It is envisioned that support portion 122 may be releasably secured to shell member 20 to permit replacement of chip member 110.

As shown, biasing portion 124 of spring assembly 120 includes a leaf spring 126 having a pair of leaf members 126a. Alternatively, biasing portion 124 may include multiple leaf springs, one or more traditional compression springs, an elastic material, or any other means capable of providing a biasing force against chip member 110.

Figure 6:
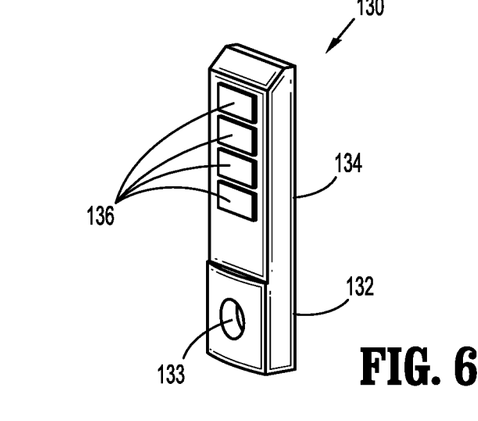
FIG. 6 is a enlarged perspective view of the connector assembly shown in FIG. 3.

With reference now to FIG. 6, connector assembly 130 includes a base portion 132 and an extension portion 134. As shown, base portion 132 defines an opening 133 configured to receive a screw 140 for securing connector assembly 130 to distal end 14b of adapter assembly 14. Although shown including opening 133 for securing connector assembly 130 to adapter assembly 14, it is envisioned that connector assembly 130 may be secured to adapter assembly 14 in any suitable manner. Extension portion 134 of connector assembly 130 includes a plurality of connection plates 136. As discussed above, connection plates 136 correspond to connection protrusion 116 formed on chip 114 of chip assembly 100. As shown, connection plates 136 define substantially flat members configured to engage rounded connection protrusions 116 of chip assembly 100. Alternately, connection protrusions 116 may be formed on extension portion 134 of connector assembly 130 and connection plates 136 may be formed on chip 114 of chip assembly 100. Connector assembly 130 is maintained in electrical communication with handle assembly 12 (FIG. 1).

Figure 7:
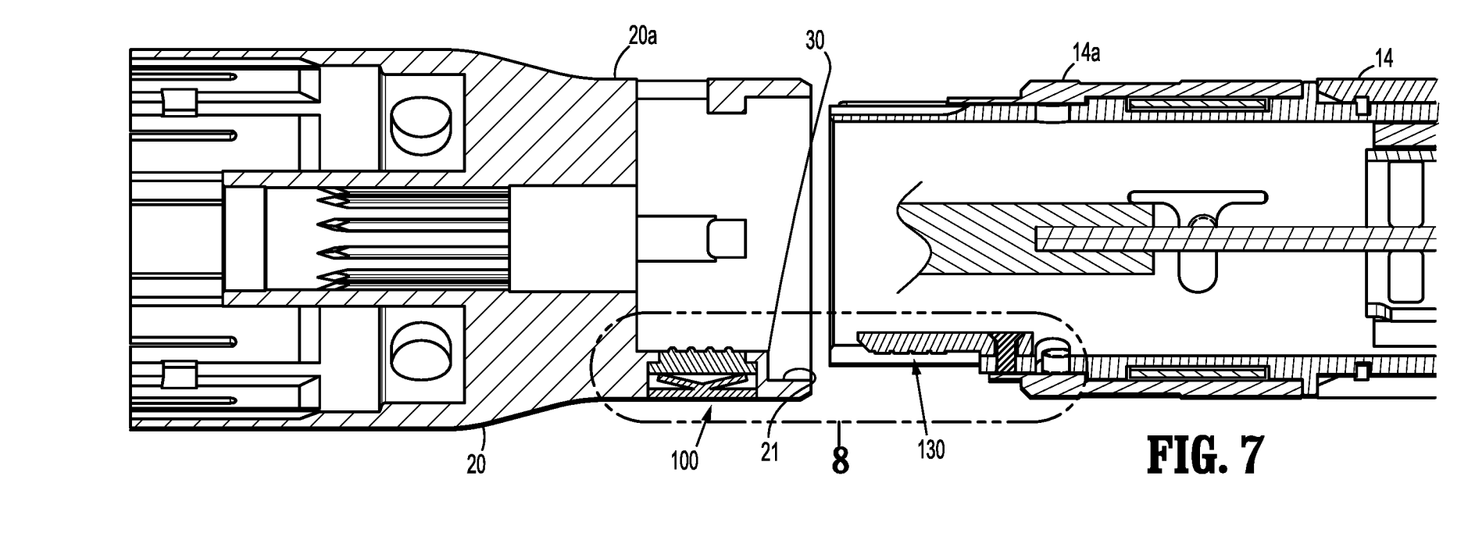
FIG. 7 is a partial, longitudinal cross-sectional side view of the loading unit shown in FIG. 2 and the distal end of the adapter assembly shown in FIG. 3, prior to attachment of the loading unit to the adapter assembly.
Figure 8:
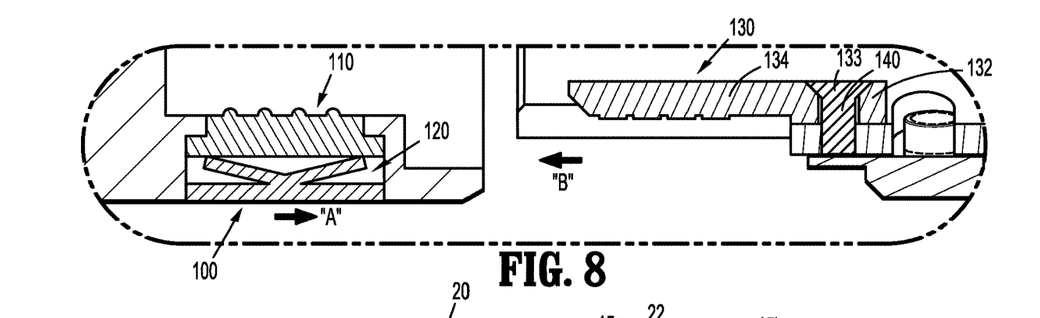
FIG. 8 is an enlarged view of the indicated portion shown in FIG. 7.

With reference now to FIGS. 7 and 8, chip assembly 100 is operably received within recess 31 of housing 30. In particular, support portion 112 of chip member 110 is radially loaded within recess 31 of housing 30 through cutout 23 formed in proximal end 20a of shell member 20. Support portion 112 is retained within recess 31 of housing 30 by engagement with lip 32. When support portion 112 engages lip 32 of housing 30, chip 114 of chip member 110 is positioned within opening 33 formed by lip 32 of housing 30 and connection protrusions 116 extend beyond lip 32.

Spring member 120 of chip assembly 100 secures chip member 110 within recess 31 of housing 30. In particular, support portion 122 of spring member 120 is received within cutout 23 of shell member 20 such that biasing portion 124 of spring member 120 biases chip member 110 radially inward. Support portion 122 of spring member 120 is secured to shell member 20 in the manner described above. As noted, it is envisioned that support portion 122 may be releasably secured to shell member 20 to permit replacement of chip member 110. Biasing portion 124 of spring member 120 permits movement of chip member 110 in a radial direction within recess 31 of housing 30 to facilitate engagement and alignment of chip member 110 with extension portion 134 of connector assembly 130. The chip is held in with the spring assembly. The leaf spring housing can be held in with a press fit, welding, etc.

With reference still to FIGS. 7 and 8, connector assembly 130 is secured to distal end 14b of adapter assembly 14 of surgical stapler 10 (FIG. 1). In particular, base portion 132 of connector assembly 130 is mounted within distal end 14b of adapter assembly 14 by screw 40 such that connection plates 136 formed on extension portion 134 of connector assembly 130 align with connection protrusions 116 formed on chip 114 of chip member 110 of chip assembly 100 when loading unit 16 is attached to distal end 14b of adapter assembly 14.

Figure 9:
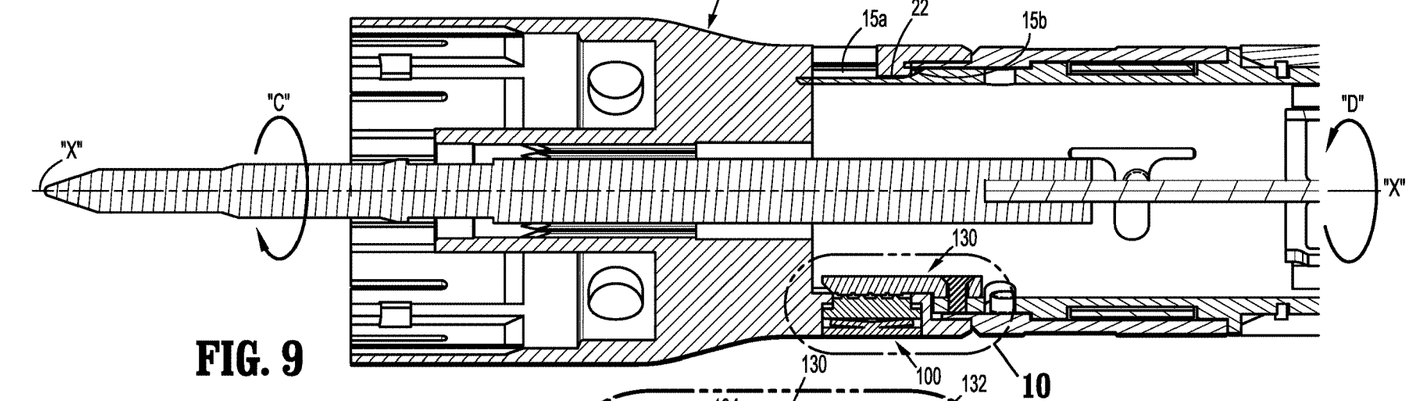
FIG. 9 is a longitudinal cross-sectional side view of the loading unit and the distal end of the adapter assembly shown in FIG. 7, subsequent to attachment of the loading unit to the adapter assembly.
Figure 10:
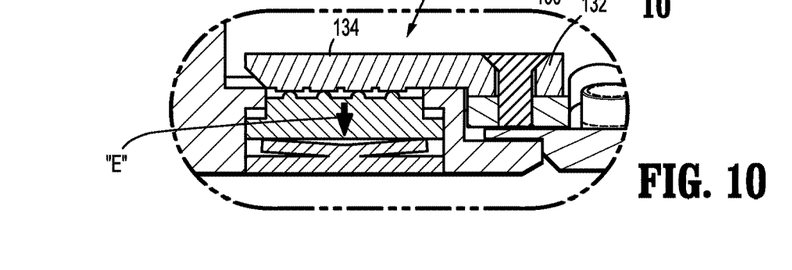
FIG. 10 is an enlarged view of the indicated portion shown in FIG. 9.

With reference now to FIGS. 9 and 10, chip assembly 100 operably engages connector assembly 130 during attachment of loading unit 16 to adapter assembly 14. In particular, and as described above, loading unit 16 is secured to distal end 14b of adapter assembly 14 by first aligning tabs 22 formed on proximal end 20a of shell member 20 with elongated portions 15a of L-shaped slot 15 formed in distal end 14b of adapter assembly 14. Shell member 20 and adapter assembly 14 are then axially advanced relative to each other, as indicated by arrows "A" and "B" (FIG. 8), respectively, such that tabs 22 formed on proximal end 20a of shell member 20 are completely received within elongate portion 15a of L-shaped slots 15 formed in distal end 14b of adapter assembly 14. Once tabs 22 are completely received within elongated portions 15a of L-shaped slots 15, the locking ring bayonet lug is rotated relative to each other about longitudinal axis "x-x". Receipt of tabs 22 of shell member 20 within shortened portion 15b of L-shaped slots 15 selectively secures shell member 20 with adapter assembly 14.

Following receipt of tabs 22 of shell member 20 within elongated portion 15a of L-shaped slot 15 formed in distal end 14b of adapter assembly 14, chip assembly 100 and connector assembly 130 are axially aligned and radially offset from one another. As such, connection protrusions 116 formed on chip 114 of chip member 110 of chip assembly 100 do not engage connection plates 136 formed on extension portion 134 of connector assembly 130.

Connection protrusions 116 formed on chip member 110 of chip assembly 100 engage connection plates 136 formed on extension 134 of connector assembly 130. As described above, connection protrusions 116 include a rounded profile to facilitate engagement of connection protrusions 116 with connection plates 136. Spring member 120 of chip assembly 100 permits chip member 110 to move radially outward, as indicated by arrow "E" in FIG. 10, to further facilitate engagement of chip assembly 100 with connector assembly 130. Once shell member 20 is secured to adapter 14 such that connection protrusions 116 of chip assembly 100 align with connection plates 136 of connector assembly 130, the biasing force provided by spring member 120 on chip member 110 biases chip member 110 radially inward to maintain engagement between connection protrusions 116 and connection plates 136.

As described above, in alternative embodiments, the attachment of loading unit 16 to adapter assembly 14 of circular stapler 10 may be accomplished by various other modes of attachment. It is envisioned that the placement of housing 30, and thus, chip assembly 100, within shell member 20 may be adjusted to accommodate the various other modes of attachment. In particular, since not all modes of attachment require rotation of shell member 20 relative to adapter assembly 14, it is envisioned that housing 30 may be positioned within shell member 20 such that chip assembly 100 aligns with connector assembly 130 upon rotating shell member 20 relative to adapter assembly 14.

Once connection protrusions 116 of chip assembly 100 are operably engaged with connection plates 136 of connector assembly 130, the information regarding the configuration of loading unit 16 that is stored on chip 114 of chip assembly 100 may be relayed to handle assembly 12 (FIG. 1) through adapter assembly 14. In this manner, handle assembly 12 may be automatically programmed to the specifications required for proper operation of circular stapler 10 and for the particular loading unit 16. Circular stapler 10 may then be used in a traditional manner.

Upon completion of a stapling procedure, loading unit 16 may be removed from adapter assembly 130 in the reverse manner from attachment. A second or subsequent loading unit (not shown), having the same or different configuration from loading unit 16, may then be attached to adapter assembly 14 of circular stapler 10 in the manner described above. It is envisioned that handle assembly 12 will automatically reprogram to accommodate the various loading units attached to adapter assembly 14.

With reference now to FIGS. 11-16, an alternative embodiment of a shell member including a chip assembly according to the present disclosure is shown generally as shell member 40. Shell member 40 is configured to receive chip assembly 200. Shell member 40 and chip assembly 200 are substantially similar to shell member 20 and chip assembly 100, and therefore, will only be described as relates to the differences therebetween.

Figure 11:
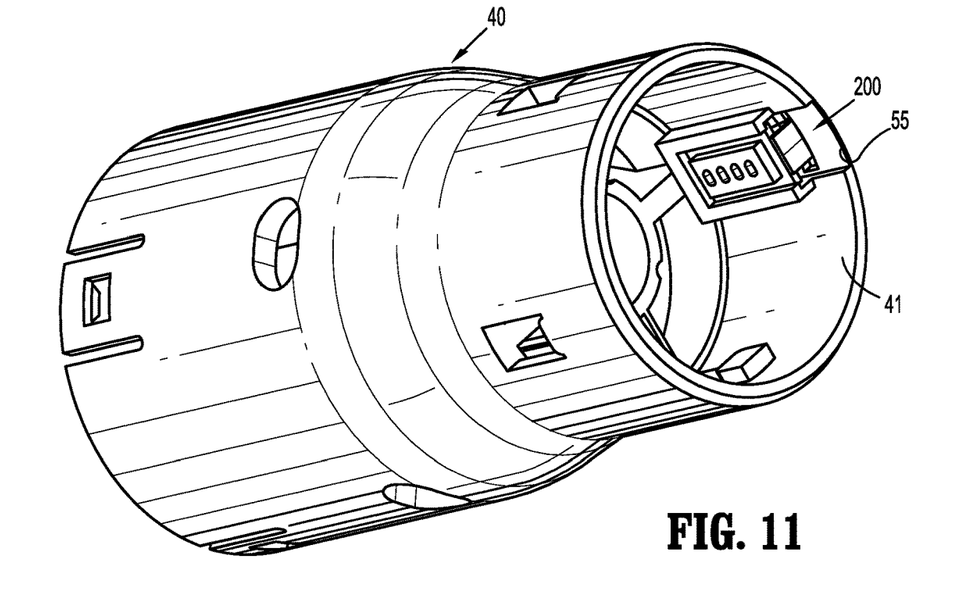
FIG. 11 is a perspective end view of a loading unit and chip assembly according to an alternative embodiment of the present disclosure.
Figure 12:
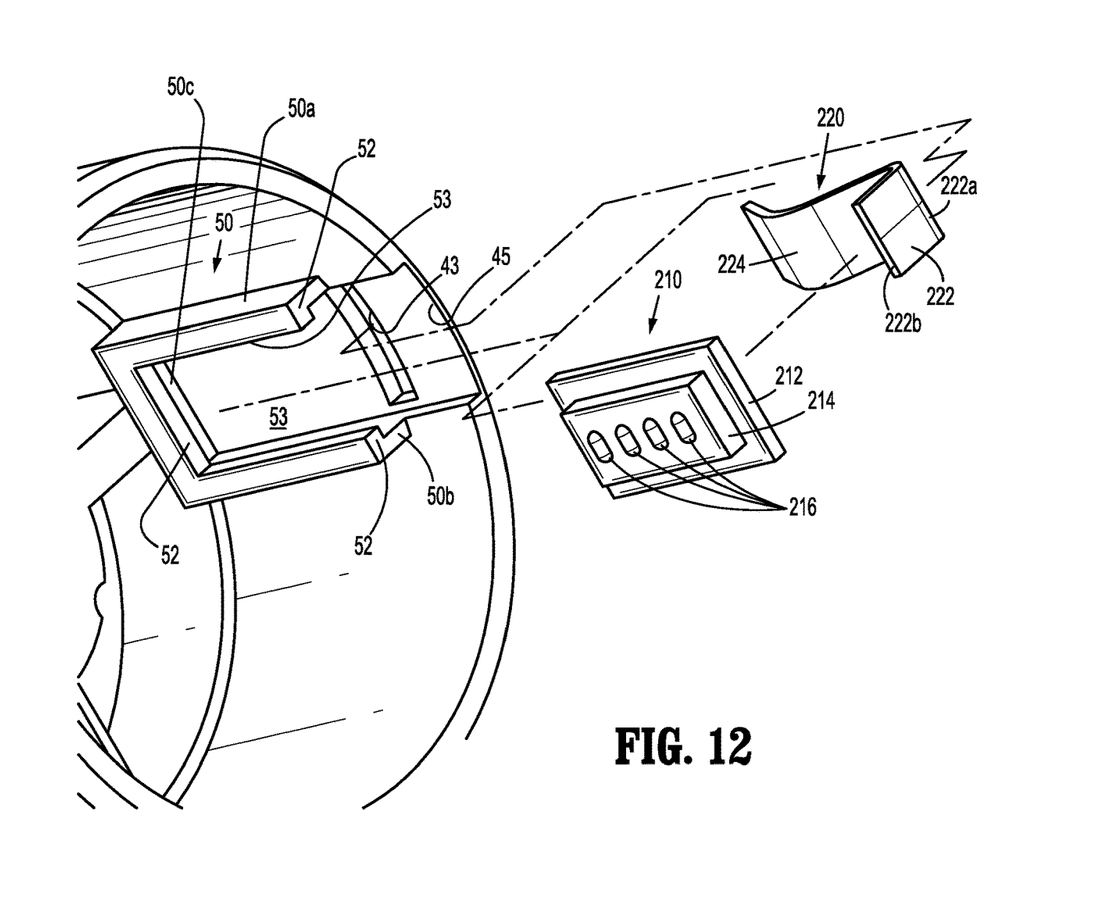
FIG. 12 is an enlarged partial perspective view of a proximal end of the loading unit shown in FIG. 11 and an exploded view of the chip assembly shown in FIG. 11.

With reference now to FIGS. 11 and 12, proximal end 40a of shell member 40 includes a housing 50 formed on an inner surface 41 thereof and defines a cutout 43 and a notch 45. Housing 50 defines a recess 51 configured to receive chip assembly 200 and includes first and second longitudinal side walls 50a, 50b, and a distal end wall 50c. A proximal end of housing 50 is open to permit axial loading of chip assembly 200 within recess 51. Notch 45 is positioned adjacent recess 53 of housing 50 and is configured to facilitate loading of chip assembly 200 within recess 53.

A lip 52 extending about first and second side walls 50a, 50b and distal wall 50c of housing 50 is provided for retaining chip assembly 200 within recess 51. Lip 52 defines an opening 53 for providing access to chip assembly 200 from within shell member 40 when chip assembly 200 is received within housing 50. Housing 50 is positioned within shell member 40 such that upon attachment of shell member 40 to distal end 14b of adapter assembly 14 chip assembly 200 aligns with a connector assembly 230 (FIG. 13) mounted within distal end 14b of adapter assembly 14. As will be described in further detail below, cutout 43 formed in shell member 40 adjacent housing 50 is configured to receive a flanged portion 222 of spring member 220 of chip assembly 200.

With reference still to FIG. 12, chip assembly 200 includes a chip member 210 and spring member 220. Chip member 210 includes a base portion 212 and a chip 214. Base portion 212 forms a planar member configured to be received within recess 51 of housing 50 formed on shell member 40. Base portion 212 is configured to permit the radial movement of chip member 210 with recess 51 of housing 50 to facilitate connection between chip assembly 200 and connector assembly 230.

Chip 214 is sized to be received through opening 53 defined by lip 52 of housing 50 formed on shell member 40. Chip 214 includes a plurality of connection protrusions 216. Spring member 220 includes flanged portion 222 and a biasing portion 224. A first end 222a of flanged portion 222 of spring member 220 is configured to be received within cutout 43 of shell member 40 and a second end 222b of flanged portion 222 of spring member 220 is configured to engage lip 52 of housing 50. As will be described in further detail below, flanged portion 222 of spring member 220 is configured to secure chip member 210 and biasing portion 224 of spring member 220 within recess 51 of housing 50. As shown, biasing portion 224 forms a curved member configured to provide a biasing force against chip member 210. The biasing force provided by biasing portion 224 against chip member 210 operably positions chip 214 of chip member 210 within opening 53 formed by lip 52 of housing 50.

Figure 13:
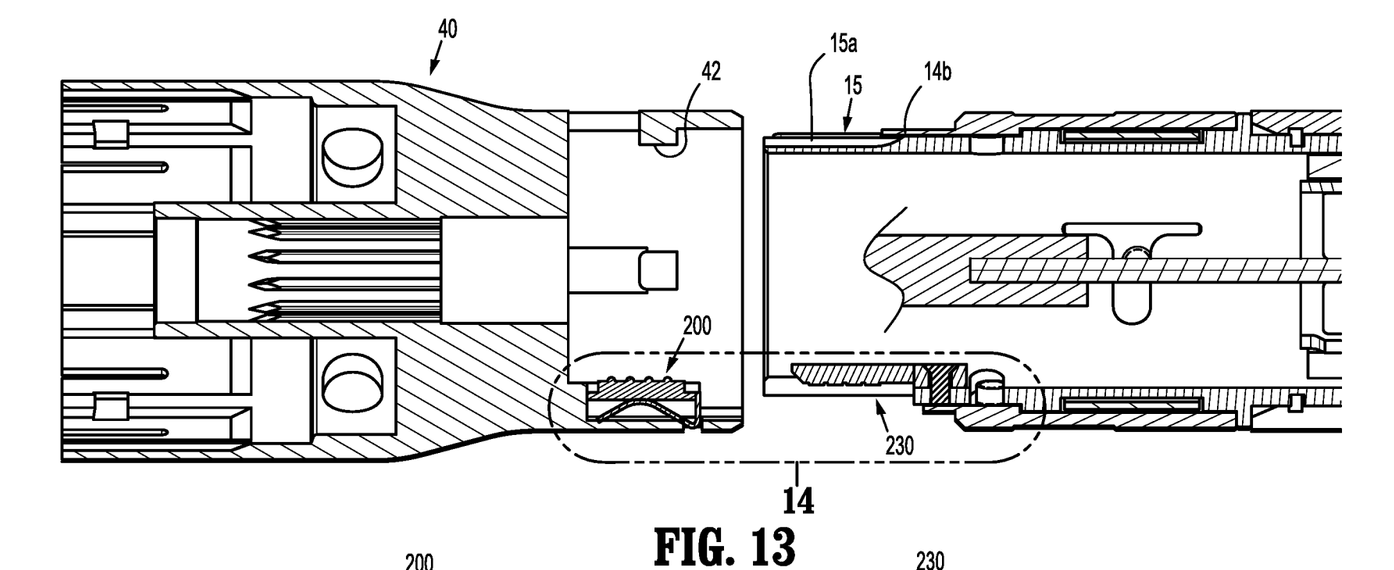
FIG. 13 is a cross-sectional side view of the loading unit shown in FIGS. 11 and 12 and the distal end of the adapter assembly shown in FIG. 3, prior to attachment of the loading unit to the adapter assembly.
Figure 14:
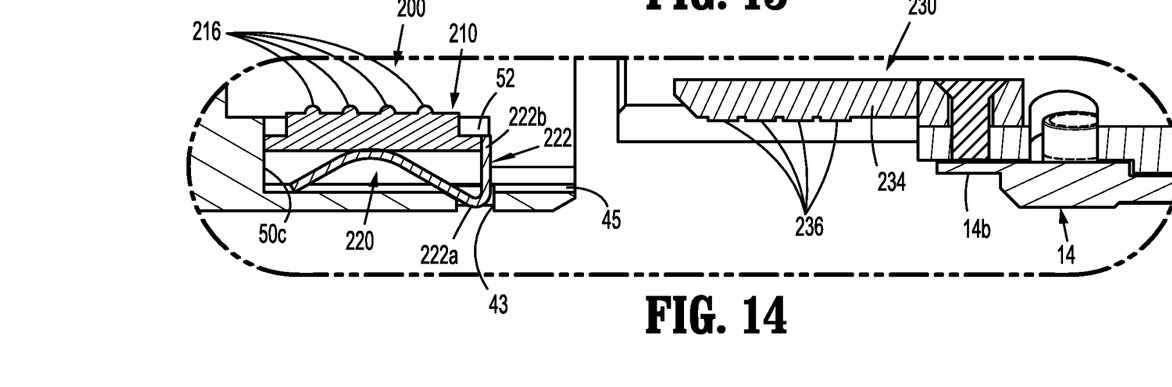
FIG. 14 is an enlarged view of the indicated portion shown in FIG. 13.

Turning to FIGS. 13 and 14, connector assembly 230 is substantially identical to connector assembly 130. Connector assembly 230 includes a base portion 232 and an extension portion 234. Extension portion 234 of connector assembly 230 includes a plurality of connection plates 236. Connection plates 236 correspond to connection protrusion 216 formed on chip 214 of chip assembly 200.

With continued reference to FIGS. 13 and 14, chip assembly 200 is operably received within recess 51 of housing 50 of shell member 40. In particular, support portion 212 of chip member 210 is received within recess 51 of housing 50 through the open proximal end of housing 50 and abuts lip 52 of housing 50. In this manner, chip 214 of chip member 210 is positioned within opening 53 formed by lip 52 of housing 50 and connection protrusions 216 extend beyond lip 52.

Spring member 220 of chip assembly 200 secures chip member 210 within recess 51 of housing 50. In particular, first end 222a of flanged portion 222 of spring member 220 is received within cutout 43 of shell member 40 and second end 222b of flanged portion 222 engages lip 52 of housing 50. In this manner, first end 222a of flanged member 222 of spring member 220 may be forced out of cutout 43 of shell member 40 to release flanged portion 222 from engagement with housing 50, thereby allowing removal of chip member 210 from recess 51 of housing 50. Although shown as being secured within housing 50 by receipt of first end 222a of flanged portion 222 within cutout 43 and engagement of second end 222b of flanged portion 222 with lip 52, it is envisioned that spring member 220 may be secured relative to housing 50 using any suitable means, e.g., bonding, mechanical fastener(s), or the spring 224 may not need a securing means (the feature 22a of spring 224 may rest on window 43 in the shell preventing proximal movement). Flanged portion 222 is secured relative to housing 50 such that biasing portion 224 of spring member 220 is received between shell member 40 and base portion 212 of base 210. Biasing portion 224 of spring member 220 permits movement of chip member 210 radially and/or axially within recess 51 of housing 50 to facilitate engagement and alignment of chip member 210 with extension portion 234 of connector assembly 230.

Figure 15:
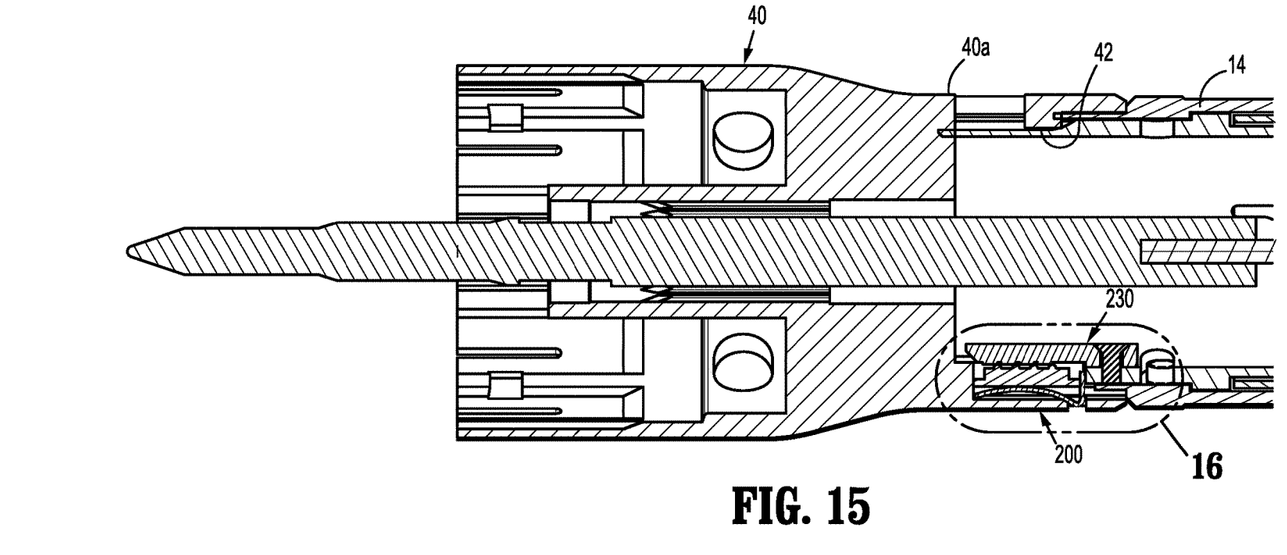
FIG. 15 is a partial, longitudinal cross-sectional side view of the loading unit and the distal end of the adapter assembly shown in FIG. 13, subsequent to attachment of the loading unit to the adapter assembly.
Figure 16:
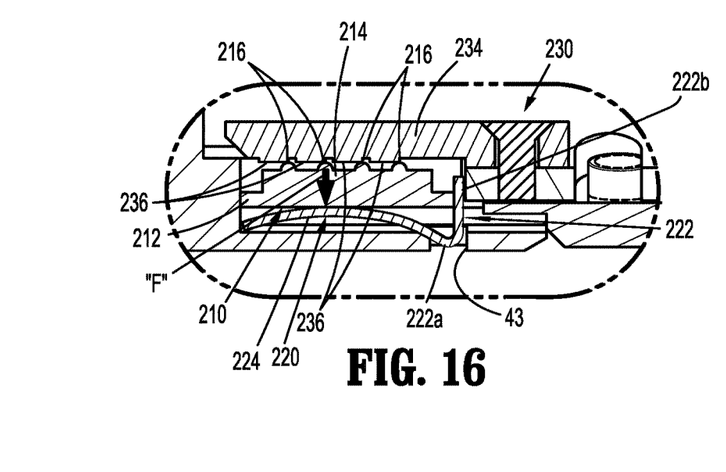
FIG. 16 is an enlarged view of the indicated portion shown in FIG. 15.

Shell member 50 is attached to adapter assembly 14 in substantially the same manner as shell member 20 is attached to adapter assembly 14. With reference now to FIGS. 15 and 16, during attachment of shell member 50 to adapter assembly 14, shell member 50 and adapter assembly 14 are axial moved relative to each other to secure tabs 42 (FIG. 11) of shell member 40 within elongated portions 15a (FIG. 3) of L-shaped slots 15 (FIG. 3) of the bayonet ring. Shell member 50 and adapter assembly 14 are then rotated relative to each other to secure tabs 42 within shortened portions 15b of L-shaped slots 15. During rotation of shell member 50 and adapter assembly 14 relative to each other, connection plates 236 on extension portion 234 of connector assembly 230 engage connection protrusions 216 on chip 214 of chip member 210 of chip assembly 200. The rounded profile of connection protrusions 216 facilitates movement of connector assembly 230 relative to housing 50. During engagement of connection protrusions 216 by connection plates 136, biasing portion 224 of support member 220 flexes to permit radial movement of chip member 210 within recess 51 of housing 50, as indicated by arrow "F", thereby further facilitating movement of connector assembly 230 relative to housing 50. Flexion of biasing portions 224 of support member 220 may also permit axial movement chip member 210 to facilitate movement of connector assembly 230 relative to housing 50.

It is contemplated that the chip assembly and connector assembly is used with a handle assembly and an adapter assembly that is removable from the handle assembly, or that the handle assembly has a permanently attached elongate portion. Although a circular stapler loading unit is described, it is contemplated that the loading unit can be a linear stapler loading unit, other types of stapler loading units, including or omitting a knife or blade for cutting tissue, or other types of surgical instrument loading units (such as, for example, electrosurgical). In addition, the loading unit and/r adapter assembly can be used with a robotic surgical system.

The contacts of the connector assembly and/or chip assembly may have a variety of shapes. They may be configured as wiper contacts or other types of contacts, and may have a leaf spring shape, U-shape, or hook-like shape.

Although the illustrative embodiments of the present disclosure have been described herein with reference to the accompanying drawings, it is to be understood that the disclosure is not limited to those precise embodiments, and that various other changes and modifications may be effected therein by one skilled in the art without departing from the scope or spirit of the disclosure.

What is claimed is:

1. A loading unit for surgical stapling device, the loading unit comprising:
    a shell member removably and selectively attachable to an elongate body portion of a handle assembly, the shell member including an inner surface;
    a staple cartridge disposed on a distal end of the shell member, the staple cartridge supporting a plurality of staples;
    a housing extending from the inner surface of the shell member; and
    a memory chip assembly disposed within the housing, the memory chip assembly being moveable relative to the shell member to facilitate connection of the memory chip assembly with the elongate body portion of the handle assembly.

2. The loading unit of claim 1, wherein the memory chip assembly includes a memory chip and a spring member.

3. The loading unit of claim 2, wherein the spring member biases the memory chip radially inward.

4. The loading unit of claim 3, wherein the spring member includes a leaf-spring for biasing the memory chip.

5. The loading unit of claim 1, wherein the housing includes a lip for retaining the memory chip assembly within a recess formed by the housing.

6. The loading unit of claim 5, wherein the lip defines an opening for selectively receiving a portion of the memory chip assembly therethrough.

7. The loading unit of claim 5, wherein the shell member defines a cutout for radial loading of the memory chip assembly into the recess formed by the housing.

8. The loading unit of claim 5, wherein the housing is configured to permit axial loading of the memory chip assembly within the recess formed by the housing.

9. The loading unit of claim 1, wherein the memory chip assembly includes a plurality of connection protrusions configured to engage a plurality of connection plates formed on a connector assembly when the loading unit is attached to an adapter assembly.

10. The loading unit of claim 1, wherein the loading unit is configured to be secured to an adapter assembly by a bayonet coupling.

11. The loading unit of claim 1, wherein the memory chip assembly includes a memory chip configured to relay a configuration of the loading unit to the handle assembly.

12. The loading unit of claim 1, wherein a connector assembly is disposed on a proximal end of the shell member for securing the loading unit to an adapter assembly.

* * * * *